United States Patent [19]

Schröer et al.

[11] Patent Number: 5,321,167
[45] Date of Patent: Jun. 14, 1994

[54] METHOD OF MANUFACTURING NONIONIC SURFACTANTS LOW IN ALKYLENE OXIDES AND LOW IN 1,4-DIOXANE, USING ALKALI METAL ALKOXIDES AS CATALYSTS

[75] Inventors: Egbert Schröer, Dorsten; Klaus Schulze, Haltern; Ekkehard Wienhöfer, Marl, all of Fed. Rep. of Germany

[73] Assignee: Huls Aktiengesellschaft, Marl, Fed. Rep. of Germany

[21] Appl. No.: 994,449

[22] Filed: Dec. 23, 1992

Related U.S. Application Data

[63] Continuation of Ser. No. 799,030, Nov. 25, 1991, abandoned, which is a continuation of Ser. No. 553,408, Jul. 17, 1990, abandoned.

[30] Foreign Application Priority Data

Jul. 17, 1989 [DE] Fed. Rep. of Germany ....... 3923562

[51] Int. Cl.$^5$ .............................................. C07C 41/03
[52] U.S. Cl. ..................................... 568/618; 568/608; 568/620; 568/648; 568/658; 568/678; 568/680
[58] Field of Search ............... 568/608, 618, 620, 648, 568/658, 678, 680

[56] References Cited

U.S. PATENT DOCUMENTS

| | | | |
|---|---|---|---|
| 3,293,193 | 12/1966 | Krahler et al. | 568/608 |
| 3,406,208 | 10/1968 | Blaser et al. | 568/620 |
| 4,453,023 | 6/1984 | McCain et al. | |
| 4,606,837 | 8/1986 | McEntire et al. | 568/608 |
| 4,973,414 | 11/1990 | Nerger et al. | 568/608 |

FOREIGN PATENT DOCUMENTS

| | | | |
|---|---|---|---|
| 544626 | 8/1957 | Canada | 568/618 |
| 0026547 | 2/1984 | European Pat. Off. | |

OTHER PUBLICATIONS

Weil et al, J. Am. Oil Chemists Soc., Mar. 1966, vol. 43 No. 3 pp. 157-160.

*Primary Examiner*—Howard T. Mars
*Attorney, Agent, or Firm*—Oblon, Spivak, McClelland, Maier & Neustadt

[57] ABSTRACT

An alkoxidation production low in alkylene oxide and 1,4-dioxane content is prepared by reacting an alkylphenol or fatty alcohol with an alkylene oxide in the presence of an alkali fatty alkoxide obtained by direct reaction of an alkali hydroxide with a fatty alcohol at elevated temperature.

11 Claims, No Drawings

METHOD OF MANUFACTURING NONIONIC SURFACTANTS LOW IN ALKYLENE OXIDES AND LOW IN 1,4-DIOXANE, USING ALKALI METAL ALKOXIDES AS CATALYSTS

This application is a continuation of application Ser. No. 07/799,030, filed on Nov. 25, 1991, now abandoned, which is a continuation of Ser. No. 07/553,408, filed Jul. 17, 1990, now abandoned.

BACKGROUND OF THE INVENTION

1. Field of the Invention

The present invention relates to a method of producing nonionic surfactants low in alkylene oxide content and low in 1,4-dioxane, by a catalytic method employing an alkali metal fatty alkoxide. It also relates to a method of production of alkali metal fatty alkoxide.

2. Discussion of the Background

Because products containing nonionic surfactants are used essentially daily, and in view of the possible toxicological hazard of appreciable impurities of alkylene oxides and 1,4-dioxane in these surfactants, it is necessary to have a supply of products having very low levels of alkylene oxides and 1,4-dioxane.

The customary production of nonionic surfactants employs catalysis with Na ions and/or K ions added to such reactants as alkylphenols, fatty alcohols, glycols, amines, fatty acids, and oils. Preferably the Na and/or K ions are added to the form of NaOH, KOH, sodium methoxide, or potassium methoxide. After establishing an inert atmosphere over the reaction medium water of solution and water of reaction are removed from the reaction medium with nitrogen. Then the reaction with added alkylene oxide is carried out.

According to U.S. Pat. No. 4,453,023 barium alkoxides can also be used as catalysts. These alkoxides are produced, according to said U.S. Patent, by reaction of barium metal with ethanol, followed by reaction with, e.g., ethylhexanol. Vacuum distillation is used to remove ethanol from the barium ethylhexanoxide which is produced.

Eur. Pat. 0 026 547 describes a similar catalyst preparation technique in which alkoxides of Ca, Sr, or Ba are prepared by reacting Ca, Sr, or Ba metal with ethanol, followed by reaction with decanol. The regenerated ethanol is then removed by applying a vacuum.

There are disadvantages associated with the method of producing nonionic surfactants according to the method described in U.S. Pat. No. 4,453,023 in which the catalyst employed is prepared by the two-step method wherein an alkali metal is reacted with ethanol, followed by reaction of the metal ethoxide with a higher alcohol. The disadvantages are very high costs, as well as a high residual content of alkylene oxides (c. 30 ppm) and 1,4-dioxane (c. 120 ppm). Further, there are problems associated with the use of metals for producing alkoxides, because of the liberation of water; and products produced with ethylhexanoxide catalysts have a strong odor of ethylhexanol. A need therefore continues to exist for a method of preparing nonionic ethoxylated surfactants low in alkylene oxides and low in 1,4-dioxane.

SUMMARY OF THE INVENTION

Accordingly, one object of the present invention is to provide a catalyst for the alkoxylation of a fatty alcohol or an alkylphenol with an alkylene oxide.

Briefly, this object and other object of the present invention as hereinafter will become more readily apparent can be attained in a method for producing alkoxidation products low in alkylene oxides and low in 1,4-dioxane by reacting an alkylphenol, a polyol or a fatty alcohol with an alkylene oxide in the presence of an alkali fatty alkoxide catalyst prepared by the direct reaction of an alkali hydroxide with a fatty alcohol at an elevated temperature.

DESCRIPTION OF THE PREFERRED EMBODIMENTS

It has now been found that the alkylene oxide content in nonionic surfactants can be reduced to <1 ppm and the 1,4-dioxane content to <3 ppm, by the use of catalysts in the surfactant preparation method which are produced according to the process of the present invention. Furthermore, the polyethylene glycol content in the adducts is <1%.

The preferred fatty alcohol for preparing the catalyst is isotridecanol. Other alcohols are polyols including ethylene glycol, propylene glycol, butylene glycol, pentylene glycol, hexylene glycol, heptylene glycol, neopentylene glycol, decylene glycol, diethylene glycol, triethylene glycol, dipropylene glycol, tripropylene glycol, pentaerythritol, galactitol, sorbitol, mannitol, erythritol, trimethylolethethane and trimethylolpropane. Others are described in U.S. Pat. No. 4,453,023. The alcohol reactant is reacted with KOH or NaOH at 100–160° C., preferably 120–140° C., normally in the absence of a solvent. However, it is possible to employ a lower alkanol solvent such as methanol or ethanol, although a distinctive feature of the invention is that a solvent does not have to be employed.

In the surfactant preparation reaction, the preferred reactants for the alkoxylation reaction are fatty alcohols of 4–24 C atoms, phenol, $C_{1-12}$ alkylphenols and propylene glycol. The alkoxylation is carried out at c. 140–200° C., preferably 160–190° C. in the absence of a solvent.

The alkylene oxide reactant is the likes of ethylene oxide, propylene oxide, butylene oxide and the like. Preferred is ethylene oxide. The amount of alkylene oxide employed as a reactant is an amount sufficient to form a product containing the desired amount of reacting alkylene oxide units.

The amount of alkylene oxide which reacts with alcohol reactant is such that the following relative amounts of alkylene oxide to alcohol reactant are employed: 0.5 to 150 moles of alkylene oxide, preferably 1 to 90 moles of alkylene oxide per mole of fatty alcohol or phenol-alkylphenol reactant, and 1 to 100, preferably 5–80 moles of alkylene oxide per mole of propylene glycol. In the alkoxylation reaction, the amount of catalyst which is present varies depending upon the amount of alcohol reactant employed. Thus, usually from 0.5 to 5 mmole of catalyst is employed per mole of fatty alcohol; from 0.025–0.1 mole of catalyst is employed per mole of propylene glycol and from 0 to 10 mmole of catalyst is employed per mole phenol-alkylphenol reactant.

Having generally described this invention, a further understanding can be obtained by reference to certain specific examples which are provided herein for purposes of illustration only and are not intended to be limiting unless otherwise specified.

EXAMPLE 1

Invention a) A 561 g amount of KOH (flake) and 2,029 g of isotridecanol were heated, with stirring, to 130° C. in a 5liter glass reactor equipped with a heater, a stirrer, and a nitrogen inlet. Stirring was continued 48 hr at 130° C. The resulting alkoxide was pourable and pumpable at 70-90° C.

b) A 561 g amount of 50% KOH and 1,014.5 g isotridecanol were mixed at 60° C. Then the emulsion was brought to reaction at 130° C. under a nitrogen atmosphere, above a thin layer evaporator, at a dropping rate 500 g/hr, wherewith water was removed. The resulting alkoxide was pourable and pumpable at 70-90° C.

EXAMPLE 2

Invention a) Using the apparatus and conditions described in Example 1a, 400 g NaOH (flake) and 2,029 g isotridecanol were charged to the reactor. The reaction mixture was stirred 72 hr at 130° C. Water byproduct was driven off with the aid of nitrogen. The resulting alkoxide was pourable and pumpable at 70-90° C.

b) A sodium isotridecanoxide was produced using a thin layer evaporator, under the conditions of Example 1b, with a startinq material of 800 g of 25% NaOH solution and 1,014.5 g isotridecanol. The isotridecanoxide was pourable and pumpable at 70-90° C.

EXAMPLE 3

Invention

A 720.9 g (3.5 mol) amount of nonylphenol and 4.08 g (12.17 mmol) K isotridecanoxide were heated at c. 60° C. in a 5-liter glass reactor with a heater, a stirrer, and a nitrogen inlet, with nitrogen purging to maintain an inert atmosphere over the reaction. Then 1,386 g (31.5 mol) ethylene oxide was added at 180° C., under an initial nitrogen pressure of 1.5 bar abs and a maximum pressure of 3 bar.

The residual content of ethylene oxide was <1 ppm, and that of 1,4-dioxane was <3 ppm.

EXAMPLE 4

Invention

A 689.5 g (3.5 mol) amount of a $C_{12}$–$C_{18}$ fatty alcohol and 1.51 g (6.34 mmol) of Na isotridecanoxide were heated to about 60° C. in the apparatus and under the conditions of Example 3, and were stirred with the purging of nitrogen gas to maintain an inert atmosphere over the reaction. Then 308 g (7 mol) ethylene oxide was added at 160° C. The residual content of ethylene oxide in the product was <1 ppm, while that of 1,4-dioxane in the product was <3 ppm.

EXAMPLE 5

Invention

A 304.8 g (4 mol) amount of 1,2-propylene glycol and 79.05 g (0.328 mol) K isotridecanoxide were heated to about 60° C. in the apparatus and under the conditions of Example 3, and were stirred with the purging of nitrogen gas to maintain an inert atmosphere over the reaction. Then 769.9 g (132.5 mol) propylene oxide was added to the reaction medium at 140° C. The residual content of propylene oxide in the product was <1 ppm.

EXAMPLE 6

Invention

A 689.5 g (3.5 mol) amount of a $C_{12}$–$C_{14}$ fatty alcohol and 1.51 g (6.34 mmol) of Na isotridecanoxide were heated to about 60° C. in the apparatus and under the conditions of Example 3. The reaction medium was stirred under a nitrogen atmosphere to maintain an inert atmosphere. Then 308 g (7 mol) ethylene oxide was added at 160° C.

The content of polyethylene glycol (PEG) was 0.4%.

EXAMPLE 7

Comparative Example

A 720.9 g (3.5 mol) amount of nonylphenol and 2.74 g (17.12 mol) 25% NaOH were stirred together as in Example 3, and water was driven off by purging with nitrogen at 130° C. Then 1,386 g (31.5 mol) ethylene oxide was added at 180° C.

The residual content of ethylene oxide in the product was 26 ppm, while that of 1,4-dioxane in the product was 118 ppm.

EXAMPLE 8

Comparative Example

As in Example 5, 304.8 g (4 mol) of 1,2-propylene glycol and 0.328 mole of Ba ethylhexanoxide (prepared according to the method described in U.S. Pat. No. 4,453,023) were heated to 60° C. and were stirred while being purged with nitrogen to maintain an inert atmosphere over the reaction. Then 7, 694.9 g (132.5 mol) propylene oxide was added to 140° C.

The propylene glycol produced did not reach the prescribed viscosity. The product had a strong odor of ethylhexanol. The residual content of propylene oxide in the product was 120 ppm.

EXAMPLE 9

Comparative Example

As in Example 6, 689.5 g (3.5 mol) $C_{12}$–$C_{18}$ fatty alcohol and 1.51 g (6.34 mmol) Ba ethylhexanoxide (prepared according to the method described in U.S. Pat. No. 4,453,023) were heated to 60° C. and were stirred while being purged with nitrogen to maintain an inert atmosphere over the reaction. Then 308 g (7 mol) ethylene oxide was added at 160° C. The content of polyethylene glycol (PEG) in the product was 2.8%.

EXAMPLE 10

Comparative Example

As in Example 4, 689.5 g (3.5 mol) of a $C_{12}$–$C_{18}$ fatty alcohol and 6.34 mmol Ba decanoxide (prepared according to the method described in Eur. Pat. 0 026 547) were heated to about 60° C. and were stirred while being purged with nitrogen to maintain an inert atmosphere over the reaction. Then 308 g (7 mol) ethylene oxide was added at 160° C. The residual content of ethylene oxide in the product was 40 ppm, and that of 1,4-dioxane in the product was 110 ppm.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the U.S. is:

1. A method of producing alkoxidation products from phenol, alkylphenols, polyols and fatty alcohols, which products are low in alkylene oxides and low in 1,4-dioxane, which comprises:
preparing an alkoxidation catalyst by combining equimolar amounts of an alkali hydroxide with a fatty alcohol and reacting these components at a temperature ranging from 100-160° C. in the absence of a solvent; and
reacting said phenol, alkylphenol, polyol or fatty alcohol with an alkylene oxide in the absence of a solvent at a temperature of 140-200° C. in the presence of said separately prepared alkali fatty alkoxide catalyst.

2. The method of claim 1, wherein sd alkali hydroxide is sodium hydroxide or potassium hydroxide.

3. The method of claim 1, wherein said fatty alcohol is isotridecanol.

4. The method of claim 1, wherein said temperature ranges from 120-140° C. in said catalyst preparation step.

5. The method of claim 1, wherein from 0.5 to 150 moles of alkylene oxide react with one mole of fatty alcohol, phenol or alkylphenol reactant.

6. The method of claim 1, wherein from 1 to 100 moles of alkylene oxide react with one mole of propylene glycol.

7. The method of claim 1, wherein from 0.5 to 5 mmole of catalyst is employed per mole of fatty alcohol.

8. The method of claim 1, wherein from 0 to 10 mmole of catalyst is employed per mole of phenol or alkylphenol reactant.

9. The method of claim 1, wherein said polyol is ethylene glycol, butylene glycol, pentylene glycol, glycol, hexylene glycol, heptylene glycol, neopentylene glycol, decylene glycol, diethylene glycol, triethylene glycol, dipropylene glycol, tripropylene glycol, pentaerythritol, galactitol, sorbitol, mannitol, erythritol, trimethylolethane or trimethylolpropane.

10. The method of claim 1, wherein said polyol is propylene glycol.

11. The method of claim 10, wherein from 0.025-0.1 mole of catalyst is employed per mole of propylene glycol.

* * * * *